US00PP14826P2

(12) United States Plant Patent
Noordhuis

(10) Patent No.: US PP14,826 P2
(45) Date of Patent: May 25, 2004

(54) PHLOX PLANT NAMED 'ELISABETH'

(50) Latin Name: *Phlox paniculata*
Varietal Denomination: Elisabeth

(75) Inventor: Bart Noordhuis, Boyl (NL)

(73) Assignee: Compass Plant Group, Lisse (NL)

( * ) Notice: Subject to any disclaimer, the term of this patent is extended or adjusted under 35 U.S.C. 154(b) by 0 days.

(21) Appl. No.: 10/437,940

(22) Filed: May 13, 2003

(51) Int. Cl.[7] ..... A01H 5/00
(52) U.S. Cl. ..... Plt./320
(58) Field of Search ..... Plt./320

*Primary Examiner*—Bruce R. Campell
*Assistant Examiner*—Annette H Para
(74) *Attorney, Agent, or Firm*—C. A. Whealy

(57) ABSTRACT

A new and distinct cultivar of Phlox plant named 'Elisabeth', characterized by its upright plant growth habit; green and pale yellow variegated leaves; freely flowering habit; and light red purple-colored flowers.

2 Drawing Sheets

Botanical classification/cultivar designation: *Phlox paniculata* cultivar Elisabeth.

BACKGROUND OF THE INVENTION

The present Invention relates to a new and distinct cultivar of Phlox plant, botanically known as *Phlox paniculata*, and hereinafter referred to by the name 'Elisabeth'.

The new Phlox is a naturally-occurring whole plant mutation of an unidentified selection of *Phlox paniculata*, not patented. The new Phlox was discovered by the Inventor in a controlled environment in Vinhega, The Netherlands, within a population of plants of the unidentified selection in 1997. The new Phlox was selected on the basis of its variegated foliage and pink-colored flowers.

Asexual reproduction of the new cultivar by vegetative cuttings taken at Vinhega, The Netherlands since February, 1998, has shown that the unique features of this new Phlox are stable and reproduced true to type in successive generations.

SUMMARY OF THE INVENTION

Plants of the cultivar Elisabeth have not been observed under all possible environmental conditions. The phenotype may vary somewhat with variations in environment such as temperature and light intensity without, however, any variance in genotype.

The following traits have been repeatedly observed and are determined to be the unique characteristics of 'Elisabeth'. These characteristics in combination distinguish 'Elisabeth' as a new and distinct cultivar:

1. Upright plant growth habit.
2. Green and pale yellow variegated leaves.
3. Freely flowering habit.
4. Light red purple-colored flowers.

Plants of the new Phlox are most similar to plants of the parent selection. In side-by-side comparisons conducted in Vinhega, The Netherlands, plants of the new Phlox differed from plants of the parent selection in the following characteristics:

1. Plants of the new Phlox had variegated foliage whereas plants of the parent selection had solid green-colored foliage.

2. Plants of the new Phlox and the parent selection differed in flower coloration.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Phlox.

The photograph on the first sheet comprises a side perspective view of a typical flowering plant of 'Elisabeth' grown in a container.

The photograph at the top of the second sheet is a close-up view of typical flowers of 'Elisabeth'.

The photograph at the bottom of the second sheet is a close-up view of the upper surface of a typical leaf of 'Elisabeth'.

DETAILED BOTANICAL DESCRIPTION

In the following description, color references are made to The Royal Horticultural Society Colour Chart, 2001 Edition, except where general terms of ordinary dictionary significance are used. Plants used in the aforementioned photographs and for the following description were grown for about three years under outdoor field conditions which closely approximate commercial production conditions in Boyl, The Netherlands. During the production of the plants, day temperatures ranged from 18 to 32° C. and night temperatures ranged from 10 to 18° C. The photographs and description were taken in July, 2002.

Botanical classification: *Phlox paniculata* cultivar Elisabeth.
Parentage: Naturally-occurring whole plant mutation of an unidentified selection of *Phlox paniculata*, not patented.
Propagation:
*Type.*—Vegetative cuttings.
*Time to produce a rooted cutting.*—About 50 days at 20° C.

*Time to produce a rooted young plant.*—About 90 days at 20° C.

*Root description.*—Thin; white in color.

Plant description:

*Form.*—Perennial; upright, conical to narrowly inverted triangle.

*Plant height.*—About 80 cm.

*Plant diameter.*—About 60 cm.

*Vigor.*—Moderately vigorous.

*Branching habit.*—Freely basal branching; about eight stems develop per plant during the flowering season.

*Flowering stems.*—Length: About 80 cm. Diameter: About 5 mm. Internode length: About 4.1 cm. Texture: Smooth, glabrous. Strength: Strong. Color: 143A to 143B.

*Foliage description.*—Arrangement: Opposite, simple. Length: About 13.8 cm. Width: About 4.1 cm. Shape: Narrowly ovate to narrowly elliptic. Apex: Acuminate. Base: Attenuate. Margin: Serrulate. Texture, upper and lower surfaces: Smooth, glabrous; slightly rugose. Venation pattern: Pinnate. Color: Developing foliage, upper surface: 137A; irregular margins, 3D. Developing foliage, lower surface: 191A; irregular margins, 3D to 4C. Fully expanded foliage, upper surface: 137A to 137B; irregular margins, 2D to 3D. Fully expanded foliage, lower surface: 191A; irregular margins, 3D. Venation, upper surface: 144C. Venation, lower surface: 138B. Petiole: Length: About 3 mm. Diameter: About 3 mm. Texture, upper and lower surfaces: Smooth, glabrous. Color, upper surface: 138B tinged with 183B. Color, lower surface: 138B.

Flower description:

*Flower type and habit.*—Single salverform flowers arranged on compound terminal panicles. Flowers face upright and outwardly. Flowers not persistent.

*Natural flowering season.*—Flowering continuous during the summer from July to August in The Netherlands.

*Quantity.*—Freely flowering with about 70 flowers per flowering stem over the entire flowering period.

*Fragrance.*—Faint, sweet.

*Flower longevity.*—About 14 days on the plant; about 10 days as a cut flower.

*Flower buds.*—Length: About 1.6 cm. Diameter: About 5 mm. Shape: Elliptic. Color, upper surface: 71A. Color, lower surface: 71C to 70D.

*Inflorescence length.*—About 10 cm.

*Inflorescence diameter.*—About 10.5 cm.

*Flower diameter.*—About 3.9 cm.

*Flower height (depth).*—About 2.4 cm.

*Petals.*—Quantity/arrangement: Five petals fused at base; rotate. Length: About 3.5 cm. Width: About 2.2 cm. Shape: Spatulate. Apex: Rounded. Margin: Entire. Texture, upper and lower surfaces: Smooth, glabrous. Color: When opening, upper surface: 58C. When opening, lower surface: 62A to 62B; tube, 71A. Fully opened, upper surface: 64C to N66C. Fully opened, lower surface: 62B to 64C; tube, 70A to 70B.

*Sepals.*—Quantity/arrangement: Five sepals fused at base; rotate, campanulate. Length: About 1 cm. Diameter: About 2 mm. Apex: Narrowly apiculate. Margin: Entire. Texture, upper and lower surfaces: Smooth, glabrous. Color: Immature and mature, upper surface: 143C; apices, 186D. Immature and mature, lower surface: 143B to 143C; apices, 187D.

*Peduncles.*—Length: About 6 cm. Diameter: About 2 mm. Angle: Erect. Strength: Strong. Color: 197B overlain with 187C to 187D.

*Pedicels.*—Length: About 4 mm. Diameter: About 1 mm. Angle: Upright to about 40° from stem. Strength: Strong. Color: 143B.

*Reproductive structures.*—Androecium: Stamen quantity: About five per plant. Anther length: About 2.5 mm. Anther shape: Oblong. Anther color: 2D. Pollen amount: Scarce. Pollen color: 2C to 2D. Gynoecium: Pistil quantity: One per flower. Pistil length: About 1.7 cm. Stigma shape: Cleft; three-parted. Stigma color: 150C. Style length: About 1.5 cm. Style color: 183D. Ovary color: 144A to 144B.

*Seeds/fruits.*—Seed and fruit development has not been observed.

Disease/pest resistance: Resistance to pathogens or pests common to Phlox has not been observed.

Temperature tolerance: Plants of the new Phlox have been observed to be tolerant to temperatures from about −20 to 40° C.

It is claimed:

1. A new and distinct cultivar of Phlox plant named 'Elisabeth', as illustrated and described.

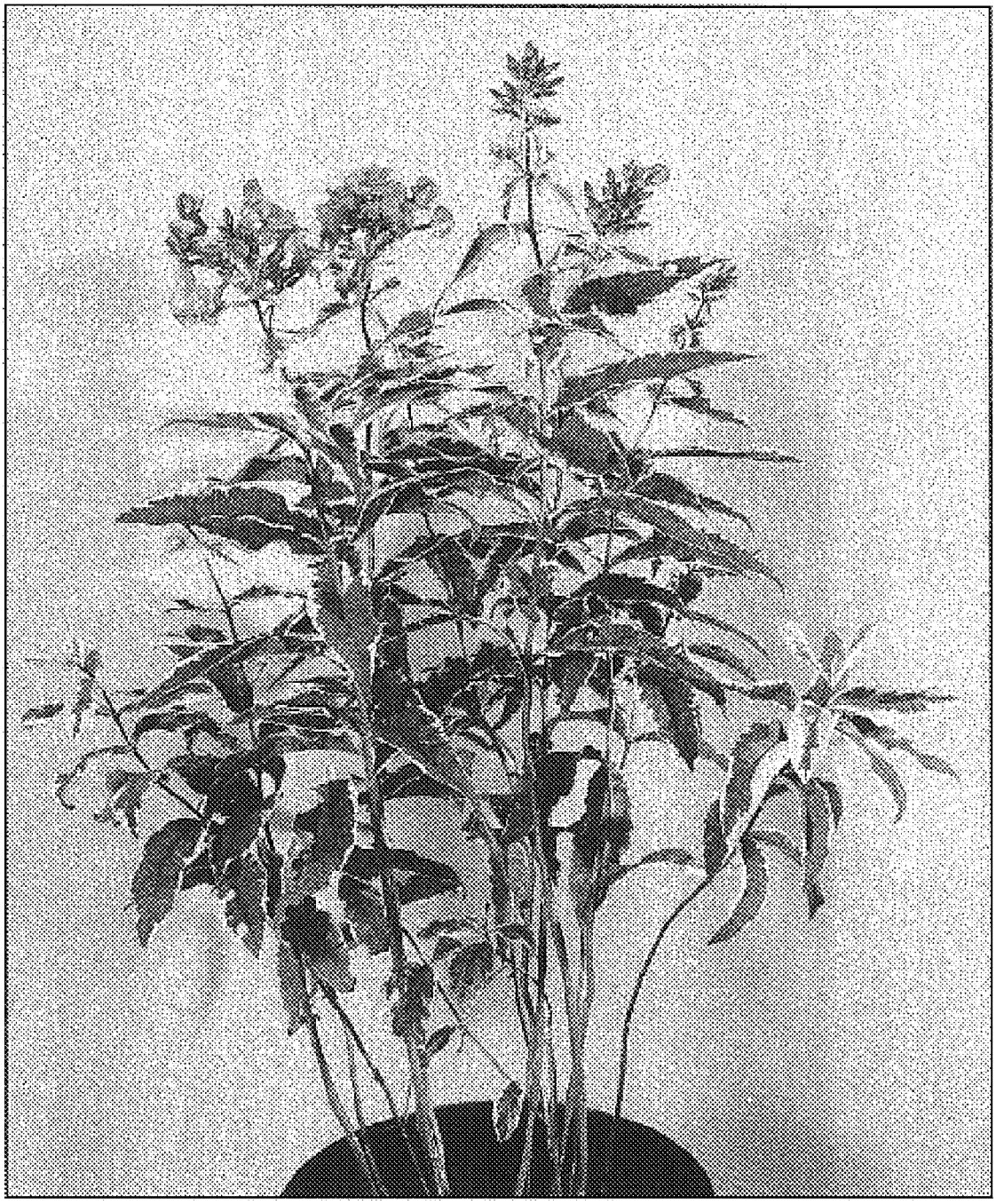

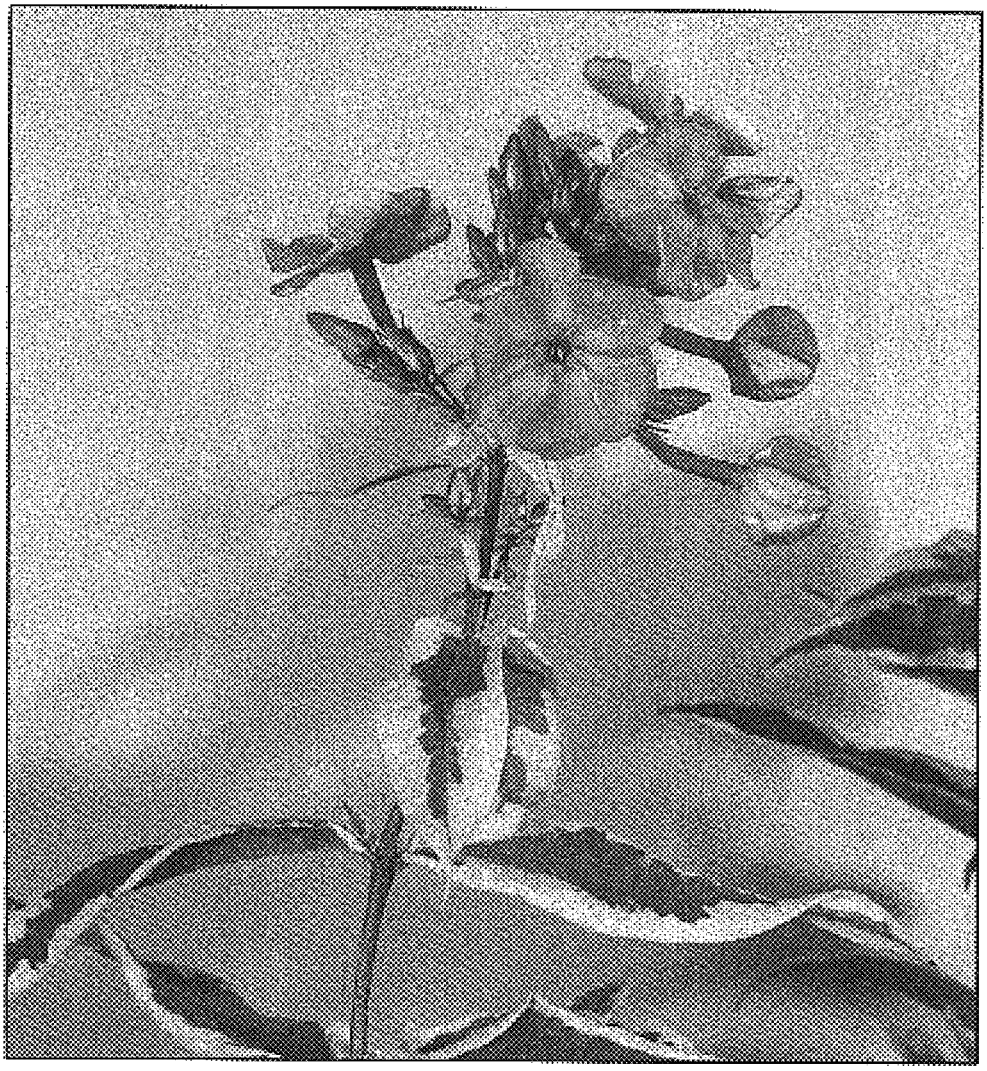
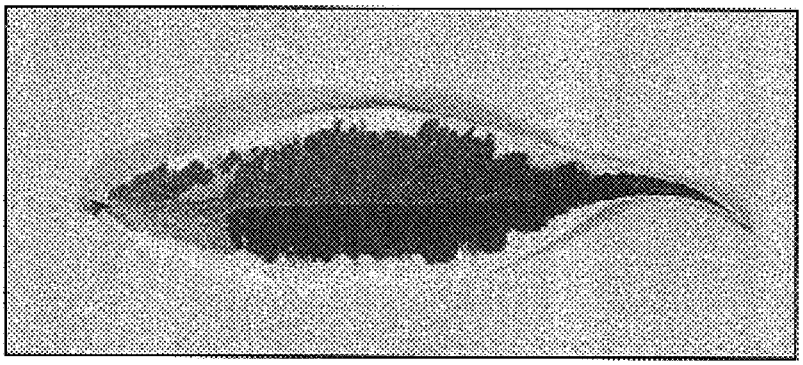

* * * * *